United States Patent
Thouppaurachchi et al.

(10) Patent No.: US 10,453,551 B2
(45) Date of Patent: Oct. 22, 2019

(54) SIMULATING LIVING CELL IN SILICO

(71) Applicant: X Development LLC, Mountain View, CA (US)

(72) Inventors: Chirath Thouppaurachchi, Mountain View, CA (US); Ian Peikon, Mountain View, CA (US); Jason Thompson, Palo Alto, CA (US); Tammo Spalink, Mountain View, CA (US)

(73) Assignee: X Development LLC, Mountain View, CA (US)

( * ) Notice: Subject to any disclaimer, the term of this patent is extended or adjusted under 35 U.S.C. 154(b) by 0 days.

(21) Appl. No.: 15/177,047

(22) Filed: Jun. 8, 2016

(65) Prior Publication Data

US 2017/0357748 A1 Dec. 14, 2017

(51) Int. Cl.
*G16B 5/00* (2019.01)
*C12M 1/00* (2006.01)
(Continued)

(52) U.S. Cl.
CPC .............. *G16B 5/00* (2019.02); *C12M 41/14* (2013.01); *C12M 41/36* (2013.01); *C12M 41/46* (2013.01);
(Continued)

(58) Field of Classification Search
CPC . C12M 1/00; G06F 19/12; C12Q 1/68; G01N 33/5005
See application file for complete search history.

(56) References Cited

U.S. PATENT DOCUMENTS

| | | | | | |
|---|---|---|---|---|---|
| 4,232,970 A | * | 11/1980 | Sawamura | ......... | G01N 15/1468 356/39 |
| 4,741,043 A | * | 4/1988 | Bacus | ................ | G01N 15/1468 348/135 |

(Continued)

FOREIGN PATENT DOCUMENTS

| | | |
|---|---|---|
| WO | 2012177150 A1 | 12/2012 |
| WO | 2014015196 A2 | 1/2014 |

OTHER PUBLICATIONS

International Search Report and Written Opinion of International Application No. PCT/US2017/036526 dated Sep. 20, 2017.
(Continued)

*Primary Examiner* — Narayan K Bhat
(74) *Attorney, Agent, or Firm* — Kilpatrick Townsend & Stockton LLP

(57) ABSTRACT

The behavior and/or internal activities of a microorganism can be simulated using a model of the microorganism. Such simulations can be used to determine the efficacy of treatments, disinfectants, antibiotics, chemotherapies, or other methods of interacting with the microorganism, or to provide some other information about the microorganism. Systems and methods are provided herein for fitting, refining, or otherwise improving such models in an automated fashion. Such systems and methods include performing whole-cell experiments to determine a correspondence between the predictions of such models and the actual behavior of samples of the microorganism. Such systems and methods also include, based on such determined correspondences, directly assessing determined discrete sets of properties of the microorganism and/or of constituents of the microorganism and updating parameters of the model corresponding to the properties of the discrete set such that the overall accuracy of the model is improved.

18 Claims, 3 Drawing Sheets

(51) Int. Cl.
*C12M 1/34* (2006.01)
*C12M 1/36* (2006.01)
*C12Q 1/02* (2006.01)
*C12Q 3/00* (2006.01)
*G01N 33/50* (2006.01)
*G01N 35/00* (2006.01)

(52) U.S. Cl.
CPC ............... *C12M 41/48* (2013.01); *C12Q 1/02* (2013.01); *C12Q 1/025* (2013.01); *C12Q 3/00* (2013.01); *G01N 33/5005* (2013.01); *G01N 33/5097* (2013.01); *G01N 35/0099* (2013.01); *G01N 35/00871* (2013.01); *G01N 2035/0097* (2013.01)

(56) References Cited

U.S. PATENT DOCUMENTS

| | | |
|---|---|---|
| 5,966,712 A | 10/1999 | Sabatini et al. |
| 5,970,500 A | 10/1999 | Sabatini et al. |
| 6,008,010 A * | 12/1999 | Greenberger .......... C12M 23/12 435/243 |
| 6,023,659 A | 2/2000 | Seilhamer et al. |
| 6,519,583 B1 | 2/2003 | Koleszar et al. |
| 6,643,634 B2 | 11/2003 | Koleszar et al. |
| 6,742,004 B2 | 5/2004 | Sabatini et al. |
| 9,068,976 B2 | 6/2015 | Putnam et al. |
| 2002/0091490 A1 | 7/2002 | Russo et al. |
| 2003/0009296 A1 | 1/2003 | Sabatini et al. |
| 2003/0084023 A1 | 5/2003 | Koleszar et al. |
| 2003/0124569 A1 | 7/2003 | Panzer et al. |
| 2004/0014087 A1 | 1/2004 | Hodgson et al. |
| 2004/0033975 A1 | 2/2004 | Fu et al. |
| 2004/0048253 A1 | 3/2004 | Panzer et al. |
| 2004/0111674 A1 | 6/2004 | Koleszar et al. |
| 2004/0158447 A1 | 8/2004 | Leger et al. |
| 2005/0095587 A1 | 5/2005 | Panzer et al. |
| 2009/0170091 A1 | 7/2009 | Giuliano et al. |
| 2010/0021959 A1 | 1/2010 | Ingham et al. |
| 2011/0216953 A1 * | 9/2011 | Callahan .................. G06K 9/00 382/128 |
| 2011/0229927 A1 * | 9/2011 | Larsen .................. C12M 21/06 435/29 |
| 2013/0151223 A1 | 6/2013 | Zamierowski et al. |
| 2014/0156050 A1 | 6/2014 | Discenzo |
| 2014/0278136 A1 | 9/2014 | Shamsheyeva et al. |
| 2015/0315546 A1 | 11/2015 | Sinha |

OTHER PUBLICATIONS

Kadir et al., "Modeling and simulation of the main metabolism in *Escherichia coli* and its several single-gene knockout mutants with experimental verification", Microbial Cell Factories, 2010, vol. 9, Article No. 88, pp. 1-21.

* cited by examiner

SIMULATING LIVING CELL IN SILICO

BACKGROUND

Unless otherwise indicated herein, the materials described in this section are not prior art to the claims in this application and are not admitted to be prior art by inclusion in this section.

A living cell, or a population of living cells, can be modeled such that the response of the living cell(s) to a variety of different environmental conditions can be quickly and cheaply estimated by simulating, using the models, the response of the cell(s) to the different environmental conditions. Such simulations can be performed to assess the efficacy of a treatment (e.g., to preserve human cells or to eliminate cancer cells or microorganism cells), to determine a configuration of an environment to improve the functioning of the cells (e.g., to produce an increased amount of an antibody or other cell product, to increase a rate of division of the cells), to determine a modification of the cell(s) (e.g., a genetic modification) to improve the functioning of the cell(s), or to provide information according to some other application. A model used to perform such simulations could be based on information that is determined about the composition or functioning of the cell(s), e.g., a model of the interaction of proteins, ions, DNA, RNA, or other metabolites or chemicals within one or more compartments within or outside of the cell(s).

SUMMARY

Some embodiments of the present disclosure provide a system including: (i) an incubator, (ii) a sensor coupled to the incubator, (iii) an automated laboratory, and (iv) a controller that is operably coupled to the incubator, the incubator sensor, and the automated laboratory. The incubator contains a microorganism and is controllable to subject the microorganism to different environmental conditions that promote or inhibit growth of the microorganism. Growth of the microorganism is associated with the microorganism taking in or releasing a substance and each instance of the microorganism includes a plurality of constituents. The sensor is operable to measure at least one external characteristic of the microorganism and the at least one external characteristic includes an amount of the microorganism in the incubator or an amount of the substance in the incubator. The automated laboratory is operable to measure at least one internal characteristic of the microorganism and the at least one internal characteristic includes an amount of one of the constituents or a degree of interaction between two or more of the constituents. The controller includes a computing device programmed to perform operations including: (1) controlling the incubator to subject the microorganism to a specified set of environmental conditions during a specified test period; (2) operating the sensor to obtain one or more measurements indicative of the at least one external characteristic of the microorganism during the specified test period; (3) accessing a model of the microorganism, wherein the model predicts a response of the microorganism to the specified set of environmental conditions during the specified test period based on a plurality of adjustable parameters; (4) determining that at least one parameter of the plurality of adjustable parameters can be adjusted such that the predicted response of the microorganism to the specified set of environmental conditions during the specified test period corresponds to the one or more measurements obtained by the sensor, wherein the at least one parameter relates to the at least one internal characteristic of the microorganism; and (5) operating the automated laboratory to measure the at least one internal characteristic of the microorganism.

Some embodiments of the present disclosure provide a method that includes: (i) subjecting a microorganism, in an incubator, to a specified set of environmental conditions that promote or inhibit growth of the microorganism during a specified test period, wherein growth of the microorganism is associated with the microorganism taking in or releasing a substance, and wherein each instance of the microorganism includes a plurality of constituents, and (ii) operating a sensor to obtain one or more measurements indicative of at least one external characteristic of the microorganism during the specified test period, wherein the sensor is coupled to the incubator, and wherein the at least one external characteristic includes an amount of the microorganism in the incubator or an amount of the substance in the incubator. The method further includes: (iii) accessing a model of the microorganism, wherein the model predicts a response of the microorganism to the specified set of environmental conditions during the specified test period based on a plurality of adjustable parameters; (iv) determining that at least one parameter of the plurality of adjustable parameters can be adjusted such that the predicted response of the microorganism to the specified set of environmental conditions during the specified test period corresponds to the one or more measurements obtained by the sensor, wherein the at least one parameter relates to at least one internal characteristic of the microorganism, and wherein the at least one internal characteristic includes an amount of one of the constituents or a degree of interaction between two or more of the constituents; and (v) operating an automated laboratory to measure the at least one internal characteristic of the microorganism.

These as well as other aspects, advantages, and alternatives, will become apparent to those of ordinary skill in the art by reading the following detailed description, with reference where appropriate to the accompanying drawings.

DETAILED DESCRIPTION

Figure 1:
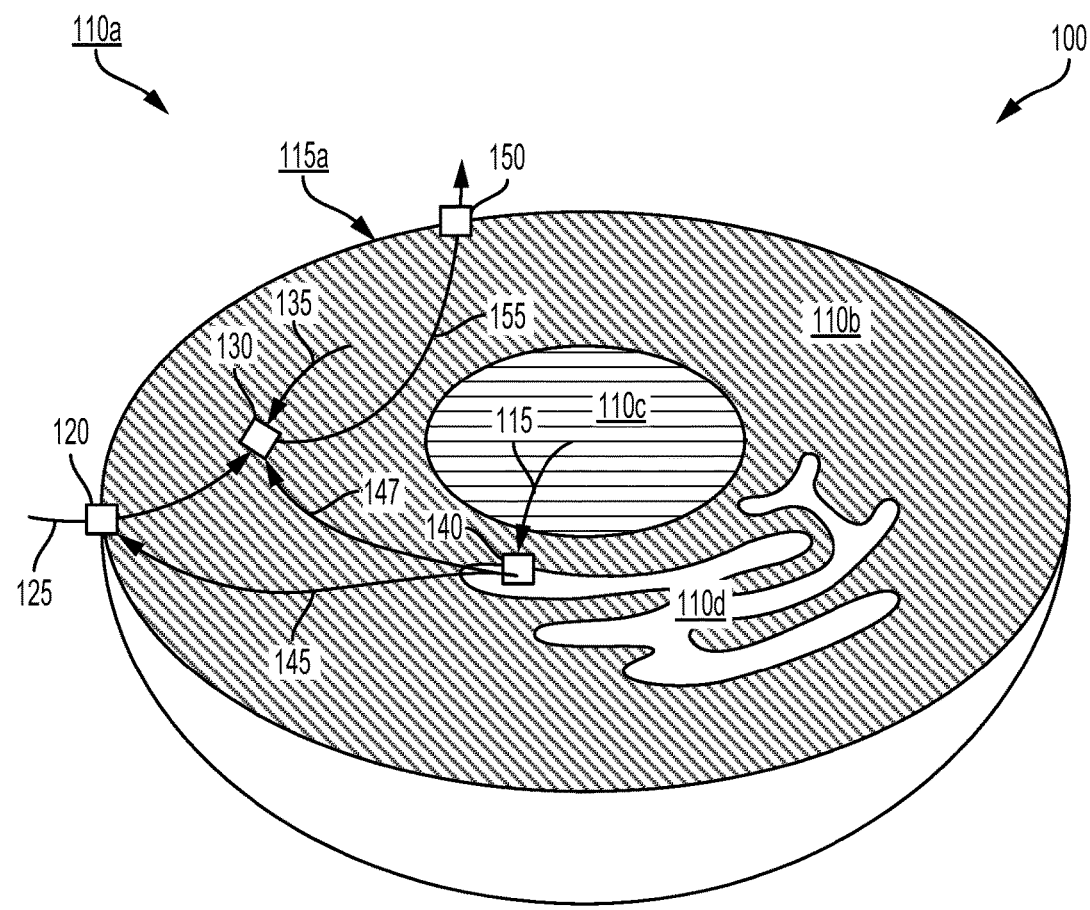
FIG. 1 illustrates an example microorganism.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations.

Further, embodiments disclosed herein make reference to microorganisms. It is contemplated that a microorganism as described herein (e.g., a microorganism with which a system described herein interacts, a microorganism that is a subject of a method described herein) may include one or more of a variety of living organisms. A microorganism, as described herein, may include any one or more of a bacterium, an amoeba, a fungus, a protest, an animal cell extracted from an animal, a cloned animal cell, a plant cell extracted from a plant, a cloned plant cell, a human cell extracted from a human, a cloned human cell, a prokaryotic organism, a eukaryotic organism, or some other microorganism. Further, a microorganism, as described herein, may include multiple genetic variants or strains of a single type of microorganism. For example, a microorganism as described herein may include multiple genetic variants of an organism that differ with respect to, e.g., one or more particular genes and/or alleles, particular nucleotides, numbers of repeats of a nucleotide sequence within a particular location of a gene, the presence or absence (e.g., knockout) of one or more genes or portions of genes, or some other genetic information. Such variants could be naturally occurring (e.g., genetic variants of a microorganism each exhibit a different naturally-occurring allele of a gene) or could be artificial (e.g., genetic variants exhibiting an artificially induced single-nucleotide polymorphism, recombinant gene(s), or other artificial genetic modifications). Methods of modeling a microorganism, as described herein, may include the modeling of a single instance of the microorganism (e.g., a single animal cell) or may include modeling a number of instances of the microorganism, e.g., that interact with each other (e.g., a colony of bacterial cells).

I. OVERVIEW

An accurate model of a microorganism (e.g., a bacterium, an amoeba, a mammalian cell, a plant cell) can allow for a variety of experiments on the microorganism to be performed quickly and cheaply in simulation. Such simulated experiments could be performed to facilitate a variety of applications. In some examples, the simulated experiments could be performed to develop an understanding of the interrelationships of various environmental and other factors on the development of the microorganism and/or on the microorganism's effect on its environment. For example, such simulated experiments could be performed to determine a set of environmental conditions that increases a growth rate of the microorganism or that increases a rate of production of a substance of interest (e.g., an antibody, a hormone, a protein, an enzyme) by the microorganism. Additionally or alternatively, the simulated experiments could be performed to develop an understanding of the effect of changes in the composition of the microorganism (e.g., changes in the genetic or epigenetic makeup of the microorganism) on the development or behavior of the microorganism and/or to develop an understanding of the effect on changes in protein structure on the functionality of such proteins. For example, such simulated experiments could be performed to determine a change in the genome of the microorganism that increases a growth rate of the microorganism or that increases a rate of production of a substance of interest by the microorganism. Such models of a microorganism, and simulations of the microorganism using such models, may be used according to other applications.

Such models of a microorganism may include many parameters, each corresponding to (e.g., 'modeling') an aspect of the structure and/or function of the microorganism. For example, a parameter of such a model could correspond to an amount and/or number of discrete instances of a constituent (e.g., a protein, a particular sequence of RNA, a metabolite, an ion) in the microorganism, a reaction rate of an enzyme, an affinity of an enzyme for a substrate or cofactor, a relationship between a DNA or RNA sequence and the function or properties of a related protein, a pH-dependence of the function of an enzyme or membrane protein, or some other properties of elements of the microorganism. The structure of such a model, and the values for such parameters of the model, may be determined based on the scientific literature. Additionally or alternatively, values of particular model parameters of interest may be determined experimentally.

The utility of such models may be related to how accurately they are able to predict the behavior of the microorganism in physical experiments. However, due to the many different parameters that may constitute such a model, it may be difficult to correct a model to more accurately predict the behavior of the microorganism, e.g., based on newly collected experimental data. In order to develop an accurate model of a microorganism, an automated system may operate to expose a microorganism to a variety of different environmental conditions (e.g., pH, light level, temperature) and/or a variety of different genetic modifications (e.g., single-nucleotide polymorphisms (SNPs), different numbers of simple sequence repeats (SSRs) at a particular location in the genome of the microorganism, selection of different alleles of a particular gene, knockouts of one or more genes or portions of genes, modification of the expression of a gene by altering promoters that control the expression of the gene) and to measure some external information (e.g., growth rate, rate of consumption of a substance, rate of production of a substance) about the response of the microorganism to such test conditions. The system could then determine a set of one or more model parameters that could be modified such that the prediction(s) of the modified model more accurately correspond to the observations made of the microorganism for the various test conditions.

The value of such candidate parameters could then be determined experimentally by the system, and the model of the microorganism updated to reflect the experimentally determined values of the selected parameters. By iterating this process (e.g., by repeating a process of incubating a sample of the microorganism, determining a set of potential parameter modifications of the microorganism model to match the observed behavior of the microorganism, experimentally evaluating the determined set of parameters, and updating the model to match the evaluation of the selected parameters), an accurate model of the microorganism may be generated.

Such a system could be configured to perform such experiments to refine a model of a microorganism without significant human intervention. That is, such a system could include robotic laboratory equipment, high-throughput screening apparatus, automated separation equipment (e.g., automated chromatography or filtration apparatus), colony pickers, digital microscopes, or other automated laboratory equipment to enable the system to incubate samples of the microorganism, to measure external properties of such incubated samples (e.g., growth rates, concentrations of analytes in within the incubators), to directly assess properties of the microorganism (e.g., amounts or counts of constituents of the microorganism) and/or of the constituents of the microorganism (e.g., affinities, reaction rates, pH-dependences of enzymes of the microorganism), or to perform some other processes to assess properties of the microorganism and/or of constituents thereof.

Further, such a process of model refinement could be performed in accordance with some additional goals. Such goals could include increasing a growth rate of the microorganism, increasing a rate of production of a substance of interest (e.g., an antibody, a protein, an enzyme) by the microorganism, increasing an efficiency with which the microorganism produces a substance of interest (e.g., decreasing an amount of sugar or other metabolites used by the microorganism to produce an amount of the substance of interest), reducing a rate of production of an unwanted substance, or some other goals. For example, the environmental conditions in an incubator and/or genetic modifications applied to the microorganism could be chosen, using the model of the microorganism, to increase the growth rate of the microorganism or to satisfy some other goal. In such an example, improvements in the accuracy of the model of the microorganism could facilitate the determination of environmental conditions and/or genetic modifications in simulation to improve the rate of growth of the microorganism, to increase the efficiency or rate of production of a substance of interest by the microorganism, or to improve some other quality of the microorganism.

It should be understood that the above embodiments, and other embodiments described herein, are provided for explanatory purposes, and are not intended to be limiting).

II. EXAMPLE MICROORGANISMS AND MODELS THEREOF

A model may be created for a microorganism or for some other system of interest in order to predict the response of the system to some input or other conditions, to develop an understanding of the behavior of the system, to optimize some interaction or intervention of the system (e.g., by repeated simulation of the system, using the model), to inspire further experiment or testing to improve the model of the system and/or to improve an overall understanding of the structure and/or behavior of the system, or to provide for some other benefit. A model may include mathematical or other descriptions of the structure and/or behavior of a system and these mathematical descriptions may be evaluated (e.g., 'simulated') to predict the behavior of the system when exposed to conditions that may also be represented mathematically in the model. For example, a model of a pendulum may include mathematical descriptions of the response of a mass of the pendulum to a local gravity field and to forces exerted on the mass by a rod or other supporting structure of the pendulum. The state of parameters and/or variables of the modeled system (e.g., the velocity and/or location of the mass of the pendulum in the example) could be determined at a number of points in time and/or in response to the modeled system being perturbed and/or interacting with an environment of interest (e.g., the velocity and location of the example pendulum could be modeled when the pendulum is exposed to a series of impulses, e.g., as from an escapement of a clock).

Such models could be used to predict the response of a system of interest (e.g., a human cell, a yeast cell, a recombinant protein-generating bacterium, or some other microorganism) to a variety of environments and/or to a variety of modifications (e.g., genetic modifications) of the system. Such predictions could be performed to determine the effectiveness of a treatment (e.g., an effectiveness of a prospective antibiotic compound against a bacterium, a toxicity of a prospective treatment to healthy human cells), to determine environmental conditions and/or genetic modifications to improve some aspect of the growth or activity of a microorganism (e.g., to increase a rate or energy efficiency or production of an antibody, protein, or other product by a bacterium), or to determine some other information about a microorganism or other system by performing simulations, using a computer or other computational substrate, rather than by performing a number of physical experiments on physical samples of the microorganism (or other system) of interest. Further, if the model has an accurate structure and/or parameters, further information about the microorganism (or other modeled system) could be determined by fitting the parameters, structure, or other properties of the model based on experimental observations or other information about the microorganism.

A model of a microorganism could include a number of parameters describing properties of the microorganism. Such parameters could be fixed during simulation of the microorganism using the model, could vary with time across a simulation, could describe an initial value and/or set point of a varying parameter or variable, or could relate to one or more properties of a microorganism in some other way. Fixed parameters could correspond to properties of a microorganism that substantially do not change over time, e.g., an association constant of an enzyme with a substrate, a reaction constant of one or more analytes into one or more product analytes, an amount of a protein or enzyme that is relatively stable over a timescale used for a simulation, or some other physical properties of elements of a microorganism and/or of subsections of a microorganism. Varying parameters could include the concentrations of analytes (e.g., ion, oxygen, ATP, metabolites), the volume of a substance within a microorganism as a whole and/or of a compartment of a microorganism (e.g., a volume of fluid within an endoplasmic reticulum of a microorganism), a concentration or amount of an analyte or product in an environment of a microorganism, a number of an enzyme, protein, section of DNA or RNA, or some other substance, or some other physical properties of elements of a microorganism and/or of subsections of a microorganism.

As described herein, a microorganism may include a variety of different living organisms and/or cells. A microorganism could include one or more instances of a bacterium, a protozoan, a fungus, an algae, a gamete of a multicellular life form, or some other unicellular organism. Alternatively, a microorganism could include one or more cells of a multicellular organism, e.g., a human cell, an animal cell, a plant cell, a cell of a fungus, a cell of multicellular algae, or cells of some other type of organism. A microorganism may include a variety of constituents, e.g., proteins, polypeptides, deoxyribonucleic acid (DNA), ribonucleic acid (RNA), nucleotides, carbohydrates, sugars, polysaccharides, ions, phospholipids, actin, myosin, or other cytoskeletal components, membranes, membrane-associated and/or -spanning proteins, organelles, vesicles, or other substances or structures composing the microorganism. The growth and/or metabolism of such a microorganism could include the microorganism taking in or releasing one or more substances (e.g., metabolites, sugars, antibodies, proteins, waste products) from or to the environment of the microorganism. Further, growth of the microorganism may include the microorganism increasing in size, dividing, budding, producing daughter cells/microorganisms, or otherwise growing and/or reproducing.

FIG. 1 illustrates, by way of example, a microorganism 100. The microorganism 100 is located within an environment 110a (e.g., a natural environment, a laboratory environment including specified amounts of one or more analytes and/or substances) and the contents of the microorganism 100 are separated from the environment 110a by a cell wall 115a. The contents of the microorganism 100 are divided by further membranes into a cytosol 110b, a nucleus 110c, and an endoplasmic reticulum 110d. Note that these divisions are intended as a non-limiting illustration of the contents and organization of a microorganism and in practice a microorganism may have more or fewer structures/contents and/or may include alternative structures/contents. For example, a prokaryotic microorganism could include substantially no subdivisions and/or membranes within its cell wall.

The proteins, membranes, enzymes, transport proteins, channels, transcriptases, ions, metabolites, phosphates, small molecules, DNA strands, RNA strands, and other constituents making up the microorganism 100 may interact in a variety of ways to effect the growth and metabolism of the microorganism 100. This could include creating substances and/or constituents of the microorganism 100 (e.g., creating additional instances of a protein from free amino acids or other substances present in the microorganism 100), destroying substances and/or constituents of the microorganism 100 (e.g., by reacting such substances with water in the microorganism 100 to hydrolyze the substances into constituent amino acids or other elements), transporting substances and/or constituents between compartments and/or regions of the microorganism 100 and/or to or from the environment 110a, forming constituents into larger structures (e.g., lysosomes, secretory vesicles, organelles, cytoskeletal structures), engaging in growth and/or reproduction, or other processes.

A model could be created to predict the behavior of the microorganism 100 within the environment 110a. Such a model could be created to model the microorganism 100 at a desired level of accuracy and/or fidelity. The level of accuracy and/or fidelity could directly represent each atom of the microorganism 100. For example, a model could be created to model each molecule and/or atom comprising the microorganism 100 such that the microorganism 100 is represented by a plurality of atoms (e.g., carbon, hydrogen, oxygen, nitrogen, phosphorus, sulfur) of the model. Alternatively, a model could be created to abstract some of the details of the microorganism 100. For example, a model could be created to model the microorganism 100 as a set of compartments (e.g., corresponding to the nucleus 110c, cytosol 110b, and endoplasmic reticulum 110d), each having respective modeled properties (e.g., volumes, osmolarities, amounts of one or more substances and/or constituents, concentration gradients within the compartment and/or between compartments). A model could be structure to abstract some aspects of a microorganism to a first level while abstracting other elements to another level. For example, a model could represent the amount of a first constituent (e.g., an ion, a small molecule, or some other quickly-diffusing substance) as a single concentration across a compartment while representing the amount of a second constituent (e.g., a large molecule, a strand of DNA or RNA, a protein, channel, or other structure that is bound to a membrane) with a concentration that varies according to location within and/or at the edge of a compartment and/or with a number of discrete instances of the second constituent that may have respective discrete locations within the modeled microorganism.

Further, a constituent could be modeled as having multiple different states. For example, an ion channel could be modeled as having three different states: 'closed,' 'open,' and 'inactivated.' The model could specify the properties of such a constituent in each of the different states and the conditions for transitioning the constituent between the different states. The model could represent such a state for each discrete instance of a constituent; alternatively, the model could abstract such information, e.g., by representing the states of a plurality of instances of such a constituent as statistically-determined populations of the constituent in each of the states, or in some derived state.

Such a model could be created to model the behavior of the microorganism 100 over time in a variety of different ways, and over a variety of different periods of time. Such a model could predict the states, configuration, behavior, or other properties of the microorganism at a plurality of discrete points in time. The timing, within a simulation using the model, of such points in time could be regularly spaced in time or determined according to some other consideration (e.g., based on the output of an adaptive solver that is configured to select more closely-spaced time points to simulate during periods of simulated time wherein faster events and/or changes are occurring in the simulated microorganism). Additionally or alternatively, aspects of the microorganism could be simulated using a continuous time variable, e.g., by determining continuous-time solutions to equations of the model that describe the structure and behavior of the microorganism. The model could describe discrete processes (e.g., binding and un-binding of a substrate or other substance to an enzyme, protein, or other ligand) and/or continuous processes (e.g., diffusion and/or mass transport within or between compartments or regions of a microorganism).

FIG. 1 illustrates a number of processes and/or constituents of the microorganism 100 that could be described by or otherwise incorporated into a model such that using the model to simulate the behavior of the microorganism 100 could result in a prediction that includes the effects of such processes and/or constituents. Arrows in FIG. 1 indicate the movement of substances and/or constituents of the microorganism 100. In a model of the microorganism 100, these movements may be represented by motion of a discrete representation of a substance, a change in a concentration or amount of a substance in a compartment or other region (e.g., a region with in a compartment) of the model and/or a corresponding decrease in a concentration or amount of the substance in another compartment or other region of the model.

This could include transfer of substances between compartments of the model. For example, the FIG. 1 illustrates movement of a strand of messenger RNA 115 from within the nucleus 110a to a ribosome 140 located on the surface of the endoplasmic reticulum 110d. In another example, FIG. 1 illustrates the movement of substances (e.g., the same substance) into the cytosol 110b from the environment 110a (125, facilitated by a channel 120 in the cell membrane 115a) and out of the cytosol 110b into the environment 110a (155, facilitated by another channel 150). These movements of substances and/or constituents between compartments of the microorganism 100 could be represented in a model by fluxes that are, themselves, determined according to concentration gradients, partition coefficients, transmembrane voltages, or other aspects of the microorganism 100 that are represented in the model. Further, such transfers and/or properties thereof could be determined based on other factors represented in the model, e.g., a number of channels present in a membrane between the compartments, the concentration of ATP or some other substance in a compartment of the microorganism 100 and/or a chemical concertation gradient between compartments to provide energy for such transfers, or some other factors.

Such channels or other factors (e.g., ATP) relating to transport of substances or constituents between compartments of the microorganism 100, as represented in a model of the microorganism 100, may be produced by constituents of the microorganism 100 and transported within to the microorganism 100 (e.g., between or within compartments, between locations on a membrane) to a membrane (e.g., 115a) or other destination. This is illustrated by example in FIG. 1, wherein the ribosome 140 produces a channel 120 (e.g., produces one or more proteins comprising the channel) that is transported 145 to the cell membrane 115a. Note that other steps and/or processes may be included in the production and transport of channels, or of other constituents or substances produced by elements of the microorganism 100. For example, one or more ribosomes may produce respective proteins (e.g., different proteins, the same protein, different isoforms of a single protein) and these produced proteins may be inserted into the lumen of the endoplasmic reticulum (ER) 110d and/or into the membrane of the ER 110d. Subsequently, the proteins may be assembled together, experience post-translational modification, experience cleavage or phosphorylation, experience addition of one or more mono- or polysaccharides, be packaged into a vesicle (within the lumen, on the vesicle wall, and/or through the vesicle wall), or some other modification and/or transport between compartments or regions of the microorganism 100. A model of the microorganism 100 may represent these processes directly and/or may abstract such processes into one or more simplifying parameters. For example, a model could represent the production of a protein or other constituent by an overall rate that is determined based on predictions or simulations of the processes underlying the protein synthesis, based on experimental measurement, or based on some other process.

A model of the microorganism 100 could include representations of the transfer of substances within compartments of the model. For example, FIG. 1 illustrates movement of a protein 130, within the cytosol 110b, from a ribosome 140 to a location in the cytosol 110b. These movements of substances and/or constituents within compartments of the microorganism 100 and/or along membranes of the microorganism 100 could be represented in a model by fluxes that are, themselves, determined according to concentration gradients, partition coefficients, transmembrane voltages, the presence of transport proteins and/or structures (e.g., cytoskeletal elements), or other aspects of the microorganism 100 that are represented in the model. Additionally or alternatively, the model could represent the amount of a substance or constituent within a compartment as a single concentration or amount (e.g., number of discrete instances of a substance), in which case transport between regions of a compartment could be represented by the model as being effectively instantaneous (e.g., for small, mobile molecules and/or for low-volume or -area compartments and/or membranes).

A model of the microorganism 100 could further include representations of the synthesis or decomposition of constituents or substances of the microorganism 100 (e.g., of proteins, DNA strands, RNA strands, enzyme, cofactors, ligands, cytoskeletal elements, substrates, or other substances or constituents of the microorganism 100), modification of constituents of the microorganism 100 (e.g., phosphorylation, cross-linking, folding, or other processes of DNA, RNA, or proteins, binding to cofactors and/or ligands), synthesis or decomposition of other substances within the microorganism 100 (e.g., generation of ATP or ADP, conversion of ATP into ADP or vice versa), or other chemical processes of the microorganism 100. For example, FIG. 1 illustrates a process facilitated by a protein 130 located in the cytosol 110b. First and second reagents and/or cofactors 135, 125 interact with the protein 130 (e.g., bind as cofactors to the protein 130, are combined by the protein 130, are expended or otherwise modified by interaction with the protein 130) to produce a product 155. The protein itself 130 is produced by the ribosome 140 transcribing a messenger RNA (e.g., 115) using amino acids, transfer RNA, and/or other substances present in the cytosol 110b and/or other compartments of the microorganism 100.

The model could describe these processes as occurring throughout a compartment of the model and/or across a membrane or other partition of the model or could represent these processes as occurring at discrete locations within a compartment and/or on a membrane or partition. The model could describe the performance of these processes in connection with enzymes, substrates, cofactors, reagents, products, or other substances. For example, the rate of production of the product 155 by the protein 130 could be determined, using the model, based on the concentrations and/or amounts of the reagents 125, 135 and the protein 130 in the cytosol 110b. Further, in instances where one or more substances or constituents involved in a process is represented by the model as a set of one or more discrete instances of the substance or constituent (e.g., wherein the model represents the process as being performed by individual instances of a particular enzyme), using the model to predict the behavior of the microorganism 100 could include predicting the performance of the process by each of the discrete instances of the substance or constituent.

Additionally or alternatively, the performance of a process (e.g., a chemical synthesis) could be abstracted in the model, e.g., an overall rate of production of a product (e.g., 155) could be determined based on a variety of other factors (e.g., amounts of enzymes, reagents, and cofactors in a relevant compartment of the model, association and dissociation constants of the enzymes, reagents, and cofactors with each other, a temperature of the environment 110a). Parameters of such an abstraction (e.g., coefficients of equations of the model used to predict the rate of production of a product based on other factors of the model) could be determined based on other information included in the model (e.g., association and dissociation constants of the enzymes, reagents, and cofactors), based on experimental observations (e.g., based on a variety of experiments conducted to measure the rate of production of a product across a variety of different conditions), or based on some other information.

Processes described in a model of the microorganism 100 could include processes transcribing DNA into RNA, transcribing RNA into polypeptides (e.g., by a ribosome), and processes whereby a polypeptide folds or is otherwise modified into a protein, enzyme, or other substance or cell constituent. Properties of a protein or other substance produced via such a transcription process could be determined, using the model, in a variety of ways. In some examples, the model could include a description of the properties of proteins produced by a discrete number of different alleles, alternative splices, or other variants of each of a set of genes of the microorganism 100. In such examples, the properties of a protein produced by transcribing a particular variant of a particular gene could be determined based on a lookup table or other means of associating information from the model description of a particular transcribed gene variant. Additionally or alternatively, the model could include information describing associations between changes in the sequence of a gene (e.g., single-nucleotide polymorphisms, the identify, location, or number of repeats of a DNA motif in a microsatellite within the gene) and changes in the properties (e.g., binding affinities to one or more substrates or substances, association or dissociation constants with reagents or other substances, time constants of reactions or other processes catalyzed by the action of the transcription product) of the protein or other constituent or substance produced by transcription or other processes related to transcription of the gene.

A model of the microorganism 100 could include descriptions of how the structure and/or behavior of the microorganism 100 and/or of elements thereof (e.g., of particular proteins, enzymes, DNA or RNA fragments, cytoskeletal elements, organelles) is affected by environmental conditions. Such environmental conditions could include temperature, osmolarity, pH, electrical currents or voltages, magnetic fields, gravity fields, stresses or strains (e.g., stresses or strains applied to the microorganism 100 and/or to elements thereof by objects or other microorganisms in the environment and/or by fluids flows in the environment), light (e.g., infrared, ultraviolet, or visible light), radio frequency signals, or other energies, substances, forces, or other conditions to which a microorganism could be exposed. Environmental conditions could include the presence of antibiotics, antibodies, radioactive substances, vaccines, chemotherapeutic substances, other microorganisms or viruses, or other objects or substances in the environment of the microorganism.

As noted elsewhere here, a model of a microorganism (e.g., 100) could model each atom, molecule, protein, or other component of the microorganism individually, or could abstract collections of such elements. A model could include such abstractions in order to accurately predict the behavior, interactions, and/or effects of the abstracted elements of the microorganism using less computational resources and/or using fewer direct measurements of the properties of each of the abstracted elements (e.g., by measuring the rate of production of a product by a set of proteins, enzymes, cofactors, and other elements of a microorganism rather than by measuring properties of each of the individual proteins, enzymes, cofactors, and other elements). Further, certain behaviors or other processes within the microorganism could be predicted and/or simulated by the model by detecting that the microorganism (or elements thereof) satisfies some conditions and, in response, changing some aspects of the modeled microorganism. A model could specify such operations in order to permit the simulation and/or prediction of specific complex behaviors or processes of the microorganism while describing the structures and processes of the microorganism at a higher level of abstraction (e.g., discrete compartments, concentrations of constituents rather than discrete constituents having respective locations and structural interconnections).

For example, a microorganism engaging in cell division may include a variety of cytoskeletal constituents aligning and/or interlocking and acting to move elements of the microorganism (e.g., chromosomes, organelles), to change a shape of the microorganism, to separate the volume of the microorganism into two or more daughter cells, or some other processes. Rather than describing and simulating the locations, interconnections, motions, and other characteristics of cytoskeletal elements of the microorganism and/or other microorganism constituents, the model could describe conditions indicative of the microorganism engaging in division (e.g., the presence of duplicate chromosomes). The model could also include a description of a set of procedures to apply to the simulated microorganism to effect changes in the simulated microorganism that approximate division (e.g., partitioning of the microorganism into two or more daughter microorganisms, expenditure of an amount of ATP or other sources of energy within the microorganism, changes in the concentration or number of constituents or substances within the daughter microorganisms relative to the parent microorganism). When simulating the microorganism, if the described conditions are present in the simulated microorganism, the set of procedures could be performed to effect division of the simulated microorganism into two or more simulated daughter microorganisms.

A model of a microorganism could be used to facilitate a variety of functions or applications. The model could be used to predict the response (e.g., growth rate, rate of generation of a product, consumption of a metabolite, or rate of generation or intake of some other substances) of the microorganism to a variety of different environmental conditions and/or genetic or other modifications to the structure of the microorganism. These predictions could be performed to test the efficacy of a substance at modifying some aspect of the function of the microorganism. For example, such predictions or simulations could be performed to assess the efficacy of a feedstock solution in facilitating production of a desired substance, to assess the efficacy of an antibiotic or antiseptic in killing the microorganism, to assess the negative effects of a substance (e.g., a chemotherapy drug) on the microorganism, to assess the efficacy of a proposed genetic modification to alter some property of the microorganism (e.g., a rate of production of a desired substance), or to determine some other information about the microorganism and/or its interaction with an environment. Such assessments, being performed by a computer using the model, may be performed more quickly and at a lesser cost than directly measuring such information experimentally using samples of the microorganism.

The elements, configurations and operations thereof, and other descriptions of a microorganism and/or model thereof herein are intended as non-limiting, illustrative examples. A microorganism could include additional or alternative elements and/or processes configured similarly or differently than those described here. A model of such a microorganism could model such elements or processes in a variety of ways and/or could model the effects and/or interactions of subsets of such elements or processes by way of abstraction, e.g., by representing the operation of a number of constituents of a microorganism by a number of parameters corresponding to the overall effects and/or interactions of such elements or processes without directly representing each element or process. Further, models and systems described herein could be configured and/or used according to the described applications or could be configured and/or used relative to some other application(s). Additional applications of models of microorganisms and systems and methods for developing, refining, and/or using such models are anticipated.

III. EXAMPLE METHODS

A model of a microorganism, as described herein, may include many parameters corresponding to properties of the structure and function of the microorganism. The utility of such a model could be related to the accuracy of predictions made using the model and/or to the verisimilitude of the model relative to the microorganism. Thus, it can be advantageous to determine accurate values for the parameters of the model.

A variety of information sources could be used to determine and/or generate the structures and/or parameter values of such a model. In some examples, information from the scientific literature could be used to determine properties of the model. This could include incorporating experimental measurements of specific physical properties of a microorganism and/or published models of elements of the microorganism (along with any experimentally or otherwise determined parameters of such models) into the model. Such information could be related to the specific microorganism of interest, to a related microorganism (e.g., a microorganism known or suspected to behave, in the context of at least one aspect of the model, similarly to the microorganism of interest), to an isolated system (e.g., to a particular metabolic process or pathway that is known or suspected to be present in the microorganism, to the activity of an isolated protein, enzyme, or other constituent(s) of the microorganism), or related to one or more aspects of the model and/or elements or processes of the microorganism in some other way.

The model may also be improved (e.g., parameters, structures, or other aspects of the model may be changed to improve the accuracy of predicted responses, made using the model, of the microorganism to one or more sets of specified environmental conditions) by performing experiments on the microorganism and/or on elements or processes of or relating to the microorganism to determine information about internal characteristics of the microorganism. Internal characteristics of a microorganism could include any characteristics or properties of the structure and/or contents of the microorganism as well as properties of the interactions between such contents. For example, an internal characteristic of the microorganism could include an amount of one of the constituents (e.g., a protein, an RNA strand having a particular sequence, a ribosome, a cofactor, ATP, a reagent, a reaction product, a channel, a receptor) of the microorganism, a degree of interaction between two or more of the constituents of the microorganism (e.g., an affinity between a protein and cofactor, a substrate, or some other substance in the microorganism, a reaction coefficient describing a reaction between reagents or other substances in the microorganism), properties of substances or constituents of the microorganism, properties of the interactions between such substances or constituents, or some other property of the structure or contents of the microorganism, of an interaction between such structures or contents, and/or of a process of the microorganism.

Performing experiments to measure internal characteristics of the microorganism could include directly measuring, by experiment, physical properties of the microorganism and/or of elements or processes of the microorganism. Measured internal characteristics could include amounts of one or more constituents or other substances in the microorganism, reaction constants of one or more chemical processes, dissociation and/or association constants of a substance in the microorganism, affinities of a ligand or other microorganism constituent for various substrates or other substances, the volume and/or osmolality of a compartment (e.g., of the nucleus) of the microorganism, or some other physical properties of the microorganism. The measured internal characteristics could be properties of particular elements or processes of the microorganism (e.g., folding geometry of a polypeptide transcribed from a particular gene or gene variant) and/or properties of sets of elements or processes or of systems of such aspects of the microorganism (e.g., parameters relating the concentration of various reagents, enzymes, cofactors, or other properties of the microorganism to the rate of production of a substance within the microorganism). These measured internal characteristics could then be used to set or update corresponding parameters of the model of the microorganism.

For example, an amount of a particular protein, sequence of DNA or RNA, or other substance or constituent in the microorganism (e.g., a baseline amount of the substance, an amount of the substance present in the microorganism when certain environmental conditions are present) could be experimentally determined (e.g., by separation of the constituents of a sample of one or more instances of the microorganism, by imaging one or more instances of the microorganism, by genetically modifying the microorganism to add a fluorescent or otherwise detectable element to the substance, and/or by some other means or processes). A parameter of the model corresponding to the measured amount (e.g., a baseline amount of the substance in the model microorganism, a rate of performance of some process in the model microorganism that corresponds to a process performed by the measured substance) could then be updated to reflect the experimentally determined amount of the substance.

To determine the parameters and/or structure of such a model, internal characteristics of each constituent and process of the microorganism could be experimentally measured. However, a microorganism may include a plurality of such constituents and/or processes such that performing such measurements for each parameter of the model is prohibitive in terms of cost, time, or some other consideration. It could be advantageous to perform such experimental measurements to determine values of particular model parameters for which determining an updated (e.g., more accurate) value may increase the accuracy of predictions of the model. Such model parameters could include parameters that are not accurately described in the literature (e.g., parameters that have been reported with wide error bars), that have been described in the literature for microorganisms that are not the same as the microorganism being modeled but whose values may be used to generate an initial model of the microorganism, that have not be described in the literature, or for which there is low confidence in the current value of the parameter. Such parameters could include parameters having large-magnitude effects on the predictions of the model such that accurately measuring the value of the parameter can increase the accuracy of microorganism behavior predicted using the model when the model has been updated to incorporate the measured value of the parameter.

Additionally or alternatively, experiments could be performed to detect some external characteristics of one or more instances of the microorganism (e.g., a cultured sample of the microorganism) when the microorganism is exposed to a variety of different environmental conditions. External characteristics of the microorganism could include a growth rate and/or amount of the microorganism (e.g., a number of instances of the microorganism, a volume of one or more instances of the microorganism) that is produced by exposure to the different environmental conditions, an amount of a substance in the environment of the microorganism (e.g., an amount of an antibody, protein, waste substance, or other substance released by the microorganism, an amount of a reagent, metabolite, sugar, or other substance taken in by the microorganism), an effect of the microorganism on the environment (e.g., an alteration of pH, a change in temperature, an emitted light), or some other property of the microorganism and/or of the interaction of the microorganism with an environment. Such external characteristics, measured across a plurality of different applied environmental conditions, could be used to fit parameters of a model of the microorganism. However, it can be difficult to determine which parameters of the model to adjust such that the model predictions the external characteristics of the microorganism correspond to the external characteristics measured by experiment. For example, the parameters of the model could be adjusted such that the model accurately predicts the experimentally measured external characteristics despite the model parameters having values that are not similar to the values of corresponding physical properties (e.g., corresponding internal characteristics) of the microorganism.

A combination of measurement of internal characteristics of a microorganism (e.g., characteristics corresponding to parameters of a model of the microorganism) and measuring external characteristics of incubated samples of the microorganism could be used to develop an accurate model of the microorganism. In particular, experiments could be performed to samples of the microorganism to one or more different environmental conditions and to measure one or more external characteristics of the microorganism when exposed to the different environmental conditions. This information could then be used to determine a discrete set of parameters of the model of the microorganism that could be adjusted such that the model more accurately predicts the measured external characteristics of the microorganism. Internal characteristics of the microorganism corresponding to these determined parameters could then be measured and the model could be updated to reflect the measurements of the internal characteristics. Such a method could have a variety of benefits in the development and/or refinement of a model of the microorganism. These benefits could include reducing a number of experimental measurements of internal characteristics of the microorganism, avoiding overfitting of the model by basing model updates on measured internal characteristics of the microorganism (rather than only based on measured external characteristics), and other benefits relative to other methods of developing and/or refining such a model.

Such a method could be performed by an automated system. Such a system could include a variety of incubators, automated laboratory equipment, sensors, imaging apparatus, chemical apparatus, robotic systems, or other elements to facilitate performance of aspects of the method with minimal or no human intervention. Further, such automated performance of the method could allow for quick, iterated performance of the method such that a model of the microorganism may be quickly refined and made more accurate relative to the actual structure and function of the microorganism.

Figure 2:
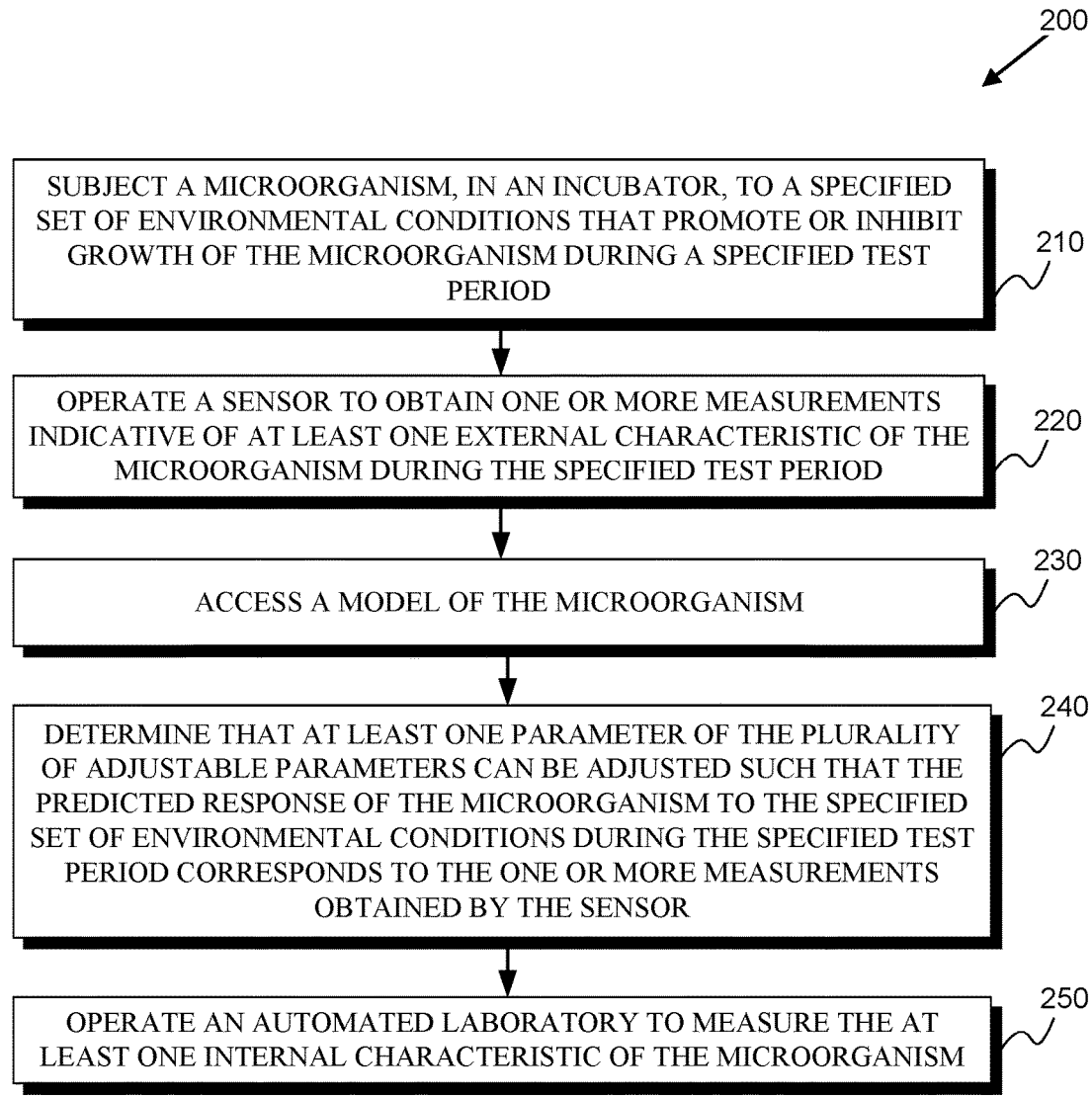
FIG. 2 is a flowchart of an example method.

FIG. 2 illustrates elements of such a method 200. The method 200 includes subjecting a microorganism, in an incubator, to a specified set of environmental conditions that promote or inhibit growth of the microorganism during a specified test period (210). Growth of the microorganism is associated with the microorganism taking in or releasing a substance (e.g., a sugar, oxygen, carbon dioxide, water, a chemical energy source, a metabolite, an ion, a vitamin, a protein, an enzyme, an antibody, a metabolic waste, ammonia, urea) and each instance of the microorganism includes a plurality of constituents (e.g., proteins, enzymes, strands of DNA or RNA, channels, receptors, actin, myosin, cytoskeletal elements, membranes, phospholipids). The substance taken in or released by the microorganism could be a constituent of the microorganism.

The method 200 also includes operating a sensor that is coupled to the incubator to obtain one or more measurements of indicative of at least one external characteristic of the microorganism during the specified test period (220). The external characteristic may include an amount of the microorganism in the incubator (e.g., a volume of one or more instances of the microorganism, a number of instances of the microorganism, a mass of the microorganism), an amount (e.g., a concentration, a mass, a volume, a number of secrete instances) of the substance that is taken in or released by the microorganism.

The method 200 further includes accessing a model of the microorganism (230). The model is capable of being used to predict a response of the microorganism to the specified set of environmental conditions during the specified test period based on a plurality of adjustable parameters. Predicting the response of the microorganism could include predicting an amount of the microorganism (e.g., predicting a growth rate, a number of instances of the microorganism, a volume or mass of the microorganism), an amount of one or more substances taken in or released by the microorganism, an effect of the microorganism on the environment (e.g., a change in pH, an amount of emitted thermal energy, an amount of emitted light energy), or some other external characteristic of the microorganism. Predicting the response of the microorganism could further include predicting a plurality of internal characteristics of the microorganism.

The method 200 yet further include determining that at least one parameter of the plurality of adjustable parameters can be adjusted such that the predicted response of the microorganism to the specified set of environmental conditions during the specified test period corresponds to the one or more measurements obtained by the sensor (240). The determined at least one adjustable parameter relates to at least one internal characteristic of the microorganism. Such internal characteristics could include an amount (e.g., a concentration, a volume, a mass, a number of secrete instances) of one or more constituents of the microorganism, a state or property of such constituents (e.g., a state of phosphorylation of a strand of DNA, a folding state of a polypeptide), a degree of interaction between two or more such constituents (e.g., a binding affinity between a ligand and a substrate), or some other internal characteristics of the microorganism. The method 200 still further includes operating an automated laboratory to measure the at least one internal characteristic of the microorganism (250) that is related to the determined at least one parameter of the plurality of adjustable parameters.

The method 200 could include further elements. For example, the method 200 could include updating the model of the microorganism based on the measured at least one internal characteristic of the microorganism (e.g., adjusting one or more parameters of the model related to the measured internal characteristic to correspond to the measured value of the internal characteristic). Additionally or alternatively, the model could be updated based on external characteristics of the microorganism measured when the microorganism is exposed to one or more different specified sets of environmental conditions. In addition to updated parameters of the model, new structures or mechanisms (e.g., metabolic pathways, means for transfer of substances between compartments of the model) could be added to the model and/or mechanisms or structures could be removed from the model based on measured internal or external characteristics of the microorganism.

The method 200 could include using the model to facilitate the determination of some information about the behavior of the microorganism when exposed to an environment of interest and/or when a genetic modification has been applied to the microorganism. For example, the method 200 could include predicting the response to the microorganism to exposure to a substance (e.g., a chemotherapy drug, an antibiotic, a growth medium) and/or to the addition or modification of one or more genes (e.g., application of one or more specified single-nucleotide polymorphisms). The method 200 could include performing a plurality of such predictions or using some other method (e.g., applying an optimization algorithm to the model) to determine a modification of an applied set of environmental conditions and/or a modification of the genome of the microorganism to improve some aspect of the behavior of the microorganism, e.g., to increase a rate or amount of a substance that is produced by the microorganism (e.g., to increase a rate of production of an antibody or of a recombinant gene product), to increase a chemical energy efficiency with which the microorganism produces such a substance, to increase or decrease a growth and/or death rate or probability of the microorganism, or to increase or decrease some other property of the behavior of the microorganism. A sample of the microorganism could then be incubated according to the determined modifications (e.g., with a modified genome and/or exposed to the modified set of environmental conditions).

Elements of the method 200 could be performed iteratively. That is, the parameters of the model could be iteratively updated based on respective rounds of measurements of external characteristics of incubated samples of the microorganism and measurements of internal characteristics of the microorganism, among other repeatedly performed elements of the method. For example, the model could be updated based on the measured at least one internal characteristic of the microorganism. The microorganism could be subjected to a second specified set of environmental conditions during a second specified test period. Further, the sensor could be operated to obtain one or more measurements of the at least one external characteristic of the microorganism during the second specified test period. The method 200 could further include determining a further at least one parameter of the plurality of adjustable parameters of the updated model could be adjusted such that the predicted response of the microorganism to the second specified set of environmental conditions corresponds to the one or more measurements obtained by the sensor during the second specified test period. The method 200 could then include operating the automated laboratory to measure the further at least one internal characteristic of the microorganism. The updated model could then be further updated based on the measured further internal characteristics and/or based on the external characteristics of the microorganism measured during the first and/or second specified periods of time.

The method 200 could include iteratively updating the model in such a way a plurality of times. The method 200 could iteratively update the model a specified number of times, until an accuracy of the predictions of the model, relative to experimental measurements of the internal and/or external characteristics of the microorganism, exceeds a specified threshold, or until some other condition is reached. In some examples, the set of environmental conditions applied to the microorganism and/or the genome of the microorganism could be specified across iterations of the method 200 to increase or decrease some property of the microorganism, e.g., to increase a rate at which an antibody, recombinant gene product, or other substance is produced by the microorganism. In some examples, the set of environmental conditions applied to the microorganism and/or the genome of the microorganism could be specified across iterations of the method 200 to improve the model in some way across the iterations (e.g., to increase an accuracy of predictions made using the model) by applying modifications to the applied set of environmental conditions and/or modifications to the genome of the microorganism between iterations to probe aspects of the model (e.g., sets of model parameters) that are uncertain and/or that have greater impact on the accuracy of the predictions of the model. Such modifications to the environmental conditions and/or genome could be determined using techniques used in machine learning, artificial intelligence, and/or system identification.

Subjecting a microorganism, in an incubator, to a specified set of environmental conditions that promote or inhibit growth of the microorganism during a specified test period (210) could include a variety of processes performed by a variety of systems. The incubator subjecting the microorganism to a specified set of environmental conditions could include subjecting the microorganism to a specified temperature, light intensity or spectrum, mechanical stress or strain, fluid flow, pressure, or some other environmental conditions. Further, the incubator could subject the microorganism to a liquid, solid, gel, or other phase of growth medium or other support substance having an osmolarity, a pH, a concentration of one or more substances (e.g., sugars, oxygen, metabolites), or some other properties according to the set of specified environmental conditions.

Subjecting a microorganism, in an incubator, to a specified set of environmental conditions (210) could include generating a sample of the microorganism and placing the sample in the incubator. This could include using one or more automated processes and/or systems (e.g., colony pickers) to move a sample of the microorganism from a source of the microorganism (e.g., from another incubator, from the same incubator, from a means for storing samples of the microorganism) into a chamber or other location or element of the incubator. Subjecting a microorganism, in an incubator, to a specified set of environmental conditions (210) could further include applying a modification to the genome of the microorganism (e.g., applying a specified SNP to the genome of the microorganism, selecting a particular variant of a gene of the genome of the microorganism, adding a gene to the genome of the microorganism) or modifying the sample of the microorganism in some other way.

The method 200 could include incubating multiple different samples of the microorganism. For example, the method 200 could include controlling the incubator, or controlling a further incubator, to subject a second sample of the microorganism to a second specified set of environmental conditions during a second specified test period (which may wholly or partially overlap in time with the first specified test period). The sensor (or a further sensor) could be operated to obtain one or more measurements indicative of at least one external characteristic of the second sample of the microorganism during the second specified test period, and determining that at least one parameter of the plurality of adjustable parameters can be adjusted such that the predicted response of the microorganism corresponds to the measurements obtained by the sensor (240) could include making such a determination such that the predicted response corresponds to the measurements obtained from both samples of the microorganism. The different samples of the microorganism could differ with respect to the genome of the microorganism. Additionally or alternatively, the different samples of the microorganism could be exposed to different specified sets of environmental conditions.

Operating a sensor that is coupled to the incubator to obtain one or more measurements of indicative of at least one external characteristic of the microorganism during the specified test period (220) could include operating a variety of different sensing means in a variety of ways. This could include detecting an amount (e.g., a number of instances of the microorganism, a mass, a volume) of the microorganism in the incubator at one or more points in time. Such detection could include optical or other non-destructive detection (e.g., using a microscope or other imaging means) and/or destructive detection (e.g., including centrifugation, chromatography, cell lysis, or other means for determining an amount of the microorganism in a sample). Such detection could include detecting an amount of the microorganism directly (e.g., visually detecting a number of instances of the microorganism, detecting an amount of absorption of an emitted light by the microorganism) or indirectly (e.g., by adding a fluorophore or other contrast agent to the microorganism and/or to a volume of the incubator containing the microorganism or by altering the genome of the microorganism to include one or more fluorescent or otherwise detectable constituents). Operating the sensor to obtain one or more measurements (220) could include detecting an amount of a substance taken in or released by the microorganism; this could include detecting a concentration of such a substance in a medium in which the microorganism is located. The detected substance could include an ion, a protein, a metabolite (e.g., a sugar, urea, ammonia, oxygen, lactic acid, carbon dioxide), an antibody, or some other substance. Operating the sensor to obtain one or more measurements (220) could include detecting a temperature, a pH, an intensity, spectrum, or other property of an emitted light, a viscosity, or some other property of the microorganism and/or of the environment in which the microorganism is located. Operating the sensor to obtain one or more measurements (220) could include obtaining more than one measurement of a single physical variable and/or obtaining one or more measurements of each of multiple different physical variables.

Accessing a model of the microorganism (230) could include a variety of computational or other processes. For example, accessing a model of the microorganism (230) could include loading the model from a data storage (e.g., via the internet or via some other means for communication). Accessing a model of the microorganism (230) could further include compiling the model into a format that can be used to generate simulations of the microorganism, e.g., to predict the behavior of the microorganism in response to a specified set of environmental conditions and/or a specified modification of the genome of the microorganism. Accessing a model of the microorganism (230) could include generating the model based on a set of information about the microorganism (e.g., based on information about the microorganism). Such information could include published experiments determining properties of the microorganism and/or of related, different microorganisms. Additionally or alternatively, accessing a model of the microorganism (230) could include modifying a generic model (e.g., a model of a generic bacterium, a model of a generic mammalian cell) to correspond to the microorganism, e.g., based on information about the microorganism and/or information about differences between the microorganism and the generic model. Accessing a model of the microorganism (230) could include additional or alternative processes.

Determining that at least one parameter of the plurality of adjustable parameters can be adjusted such that the predicted response of the microorganism to the specified set of environmental conditions during the specified test period corresponds to the one or more measurements obtained by the sensor (240) could include a variety of different processes. Adjusting at least one parameter of the model such that predicted response of the microorganism corresponds to measurements obtained by the sensor could include adjusting the at least one parameter such that the predicted response is closer in value to the measured external characteristic. This could include adjusting the at least one parameter such that a plurality of predicted external characteristics (e.g., predicted concentrations of a plurality of different substances taken in or released by the microorganism) correspond to measurements obtained by the sensor. Such correspondence could be assessed by a linear or nonlinear cost function that receives the predicted measurement values and the sensor-obtained measurement values as inputs. Further, in examples wherein multiple samples of the microorganism are incubated and measured, such a correspondence could be determined across the measured external characteristics of the multiple samples.

Determination and/or selection of the at least one parameter could be performed in a variety of ways. Such determination could be based on a measured or otherwise determined uncertainty for each of the parameters. Such an uncertainty could be based on the scientific literature (e.g., based on the width of one or more reported possible ranges for a measured parameter and/or based on a degree of different between reported values of the parameter), on previous measurements of internal and/or external characteristics of the microorganism (e.g., using techniques provided by machine learning, artificial intelligence, and/or system identification), or on some other consideration. In such examples, a particular parameter could be less likely to be determined if the uncertainty in the value of the particular parameter is less; that is, parameter values that have lower uncertainty could be less likely to be directly measured. Determination and/or selection of the at least one parameter could be based on a cost of assessing a related internal characteristic of the microorganism. For example, parameters related to internal characteristics of the microorganism that are more difficult and/or more expensive to measure could be less likely to be selected than model parameters related to easily-measured internal characteristics of the microorganism. In some examples, a degree of accuracy of measurement of the determined at least one parameter could be determined, and one or more related internal characteristics of the microorganism could be measured to an accuracy and/or sensitivity sufficient to measure the determined at least one parameter to the specified degree of accuracy.

Operating an automated laboratory to measure the at least one internal characteristic of the microorganism (250) that is related to the determined at least one parameter of the plurality of adjustable parameters could include a variety of processes, implemented by a variety of systems of an automated laboratory. This could include determining a concentration, a volume, a mass, a discrete number of instances of the constituent, or some other measure of the amount of the constituent in the microorganism as a whole, in one or more compartments or regions of the microorganism, as a distribution over volume and/or area of the microorganism, or according to some other consideration. Additionally or alternatively, measuring the at least one internal characteristic of the microorganism (250) could include determining a degree of interaction between two or more of the constituents of the microorganism. This could include determining an affinity of binding between two or more substances (e.g., between an enzyme an a cofactor, between an enzyme and a reagent or substrate of a reaction facilitated by the enzyme, between a receptor and a ligand, between two proteins, between subunits of a channel, receptor, ribosome, or other constituents of the microorganism), a reaction rate or other property of a reaction between two or more substances, an association or dissociation constant of two or more substances, or some other information about the interaction between two or more elements that may be found in the microorganism.

Measuring the at least one internal characteristic of the microorganism (250) could include measuring some other information about the structure or function of the microorganism. Measuring the at least one internal characteristic of the microorganism (250) could include measuring some other information about the configuration or function of the microorganism and/or of constituents or substances thereof, e.g., determining an optical property of a fluorophore, a folding state or geometry of a polypeptide, a folding state or geometry of a strand of RNA, a phosphorylation state of a strand of DNA, properties of a channel (e.g., a relationship between concentration gradients, the presence of a receptor, a potential difference, or some other factors and the rate of flux of one or more substances through the channel), or some other information about the microorganism.

Measurement of certain internal characteristics of the microorganism could include measuring properties of constituents or substances of the microorganism in isolation or otherwise outside of an instance of the microorganism. That is, constituents of the microorganism and/or other substances that may be found in the microorganism could be provided outside of the microorganism (e.g., in a reaction vessel, in a culture dish, in a different microorganism) and one or more properties of the substances (e.g., a reaction rate, a pH-dependence of some property of the substances, and affinity between a ligand and some other substance, a temperature-dependence of some property of the substances) could be measured. The constituents or substances used in such a measurement could be received from means for storing such substances (e.g., a material storage carousel or other element(s) of an automated laboratory or from containers in a stockroom) or could be derived from a sample of the microorganism. For example, a sample of the microorganism (or of a different microorganism) could be lysed, separated (e.g., via chromatography, centrifugation, or some other separating means), chemically reacted, or otherwise treated to provide a source of materials used to measure an internal characteristic of the microorganism. Alternatively, such internal characteristics could be measure in one or more instances of intact microorganisms, e.g., by fluorescent or other imaging means, by calorimetry, or my some other means of measuring properties of substances or processes located and/or occurring within an instance of the microorganism.

Measuring the at least one internal characteristic of the microorganism (250) could include measuring an internal characteristic directly (e.g., directly measuring a volume or area of the microorganism and/or of a compartment or region of the microorganism using imaging or other means) or indirectly. Indirectly measuring an internal characteristic could include measuring a physical variable that is related to the internal characteristic. This could include measuring an amount of a product of a reaction in order to indirectly measure a characteristic of the reaction and/or of an enzyme or reagent involved in the reaction, measuring a substance that is a produced via a process that uses, as an input, a product of a reaction in order to indirectly measure a characteristic of the reaction and/or of an enzyme or reagent involved in the reaction, or measuring some other property or properties to determine some information about an internal characteristic of the microorganism.

Indirectly measuring an internal characteristic of the microorganism could include performing a reaction or process on the microorganism and/or constituents thereof. For example, a process of polymerase chain reaction or some other process could be performed to increase an amount of DNA, RNA, of a particular sequence or strand of DNA or RNA, or of some other constituent of the microorganism and the increased amount of the constituent could be measured in order to determine an amount of the constituent in the microorganism.

Indirectly measuring an internal characteristic of the microorganism could include adding a contrast agent, reporter, or other substance to facilitate detection of the internal characteristic. For example, a fluorescent reporter could be added to one or more particular constituents to facilitate fluorescent imaging of the constituents to, e.g., determine a number, amount, location, or distribution of the constituent in the microorganism, to determine a degree of interaction between two or more of the labeled constituents (e.g., via imaging of Forster resonance energy transfer between fluorophores of the two or more labeled constituents), or to determine some other information about the microorganism. Adding a contrast agent, reporter, or other substance to the microorganism and/or to constituents of the microorganism could include adding a fluorophore, adding a fluorescent substance that is configured to selectively interact with (e.g., bind to, react with) a substance of interest, genetically modifying the microorganism to produce a version of a constituent that includes a fluorescent element, or some other processes.

Measuring the at least one internal characteristic of the microorganism (250) could include measuring an effect or relationship between a sequence of DNA or RNA and one or more properties of other constituents of the microorganism, e.g., of a protein generated by transcription of the DNA or RNA. This could include determining the effects of a particular SNP, motif repeat, alternative transcription, gene variant, or other modification of the genome of the microorganism on properties of a protein, enzyme, channel, ribosome, or other constituent of the microorganism produced by the transcription and/or folding of the DNA or RNA sequence related to the modification of the genome. Measurements of such internal characteristics could facilitate the development of aspects of the model of the microorganism that relate the sequence or other information about the genome of the microorganism to other properties of the microorganism (e.g., binding affinities of enzymes, receptors, channels, or other proteins or constituents of the microorganism). Performing such measurements could include inducing one or more modifications of the genome of the microorganism in respective samples of the microorganism (e.g., via knockout, recombination, floxing, or some other techniques for genetic manipulation) and performing measurements of properties of each of the samples of the microorganism and/or of separated elements of each of the samples of the microorganism (e.g., organelles, proteins, enzymes, channels, membrane fragments, folded RNA strands).

The method 200 could include additional or alternative blocks to those shown in FIG. 2. A model developed using the method 200 could be used for a variety of applications.

IV. EXAMPLE SYSTEM

The methods described herein could be performed by a system including extensive automation, such that human intervention may be minimized. Such a system could perform iterated experiments to measure internal and external characteristics of a microorganism of interest and to refine a model of the microorganism based on such measurements. Such a system could include automated incubators, laboratory equipment, robotics, or other systems to facilitate the performance of such measurements. Such a system could receive inputs of materials (e.g., chemical reagents, proteins, antibodies) and/or may produce materials, e.g., by incubating samples of the microorganism or of some different organism and extracting the materials from such incubated organisms and/or by performing chemical reactions or other processes on materials that are available to the system. Elements of such a system could be located in a single location (e.g., a single building, a single room, a single shipping container) and/or may be located in a plurality of different locations and configured to communicate with each other to facilitate operations of the system (e.g., to facilitate control of, and to receive measurements or other information from, incubators, automated laboratory equipment, sensors, or other elements of the system).

Figure 3:
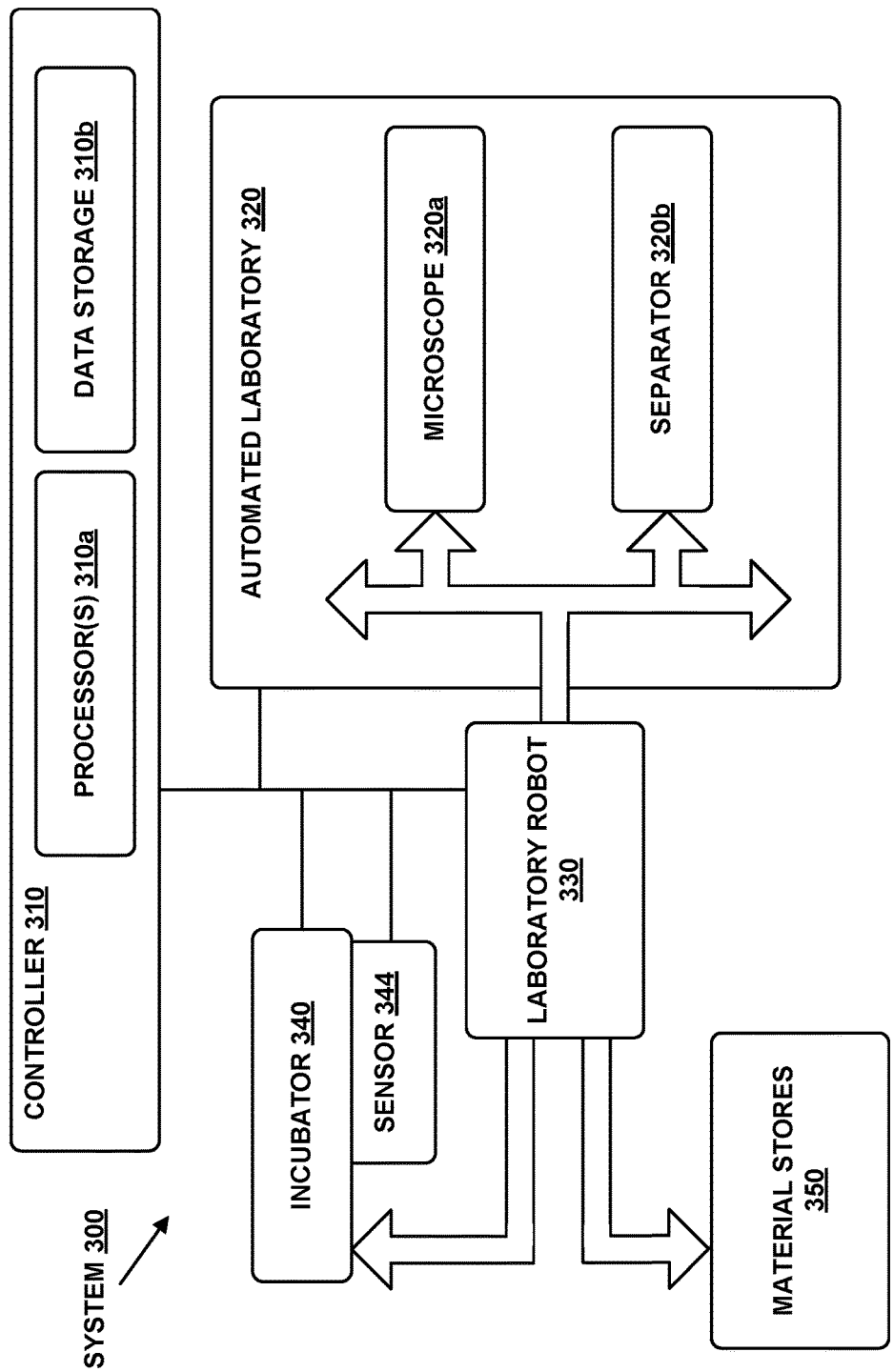
FIG. 3 is a functional block diagram of an example system.

FIG. 3 is a simplified block diagram illustrating the components of such a system, according to an example embodiment. The system 300 may take a variety of forms. For example, the elements of the system 300 could be located in a single location, e.g., within a shipping container or other easily transported means. Alternatively, elements of the system 300 may be located in different locations and placed into communication with each other, e.g., over the Internet. In a particular example, certain elements of the controller 310 or other computational elements of the system 300 could be provided as part of a cloud computing system. The system 300 also could take other forms.

In particular, FIG. 3 shows an example of a system 300 having a controller 310, an incubator 340, a sensor coupled 344 to the incubator 340, an automated laboratory 320, a laboratory robot 330, and material stores 350. The automated laboratory 320 includes a microscope 320a and a separator 320b, but may include additional or alternative elements. Further, the system 300 may include additional or alternative elements to those illustrated in FIG. 3, e.g., multiple instances of one or more of the elements, one or more communications interfaces, a user interface, or some other elements.

The incubator 340 is controllable to subject the microorganism (e.g., to subject one or more samples of the microorganism) to different environmental conditions that promote or inhibit growth of the microorganism. This could include providing, to a culture dish or other receptacle for a sample of the microorganism, a controlled temperature, light level, fluid flow, or other conditions. The incubator 340 subjecting the microorganism to different environmental conditions could include providing a culture medium (e.g., a liquid, solid, gel, or other material for supporting a sample of the microorganism) having a number of specified properties, e.g., a viscosity, an osmolarity, a pH, a concentration of one or more substances (e.g., sugars, oxygen, alcohols, chemotherapeutics or other pharmaceuticals, antibiotics), a presence of one or more other microorganisms, or some other specified properties. The incubator could include a colony picker or other means for transporting, removing, and/or otherwise interacting with samples of the microorganism and/or preparing environments (e.g., culture mediums and/or dishes) for the microorganism.

Samples of the microorganism incubated in the incubator 340 could be provided from the incubator 340 itself, from the material stores 350, or from some other source. The material stores 350 could include stored samples of the microorganism, of other materials used to incubate the microorganism in the incubator 340 (e.g., samples of growth media, metabolites, gases, means for genetically modifying samples of the microorganism), stored samples of other microorganisms (e.g., microorganisms that could be used to produce materials to incubate the microorganism in the incubator 340 and/or to measure some internal or external characteristics of the microorganism using the sensor 344 and/or automated laboratory 320), or other substances. Such materials could be transported between and/or within the material stores 350, incubator 340, automated laboratory 320, or other elements of the system 300 using the laboratory robot 330. The laboratory robot 330 could include pipettors, colony pickers, high throughput screening robots, robotic arms or armatures, tracks and/or chassis for moving elements of the laboratory robot 330 between elements of the system 300, carousel storage and/or incubation systems (that could additionally or alternatively be part of the incubator 340, material stores 350, or other elements of the system 300), or other elements or apparatus.

In another example, the automated laboratory 320 could be used to generate and/or prepare samples of the microorganism. This could include incubating samples of the microorganism, dividing or partitioning a sample of the microorganism (e.g., to select instances of the microorganism having desired characteristics), causing alterations to the genome of a sample of the microorganism (e.g., by exposing a sample of the microorganism to a retrovirus, a plasmid, or some other genome-altering substances), or by performing some other incubation and/or sample preparation processes.

The sensor 344 is configured to measure at least one external characteristic of the microorganism. This could include detecting one or more properties of the microorganism when the microorganism is located in the incubator, e.g., using imaging to determine an amount of the microorganism at one or more points in time, an amount of an optically-detectable substance within the microorganism and/or in the environment of the microorganism (e.g., of a fluorescent reporter that is configured to bind to a substance of interest), or to determine some other external characteristic of the microorganism. Additionally or alternatively, detecting an external characteristic of the microorganism could include providing a substance from the incubator (e.g., an amount of a sample medium, a sample of the microorganism that has been centrifuged or otherwise treated) to the sensor 344. In such examples, the sensor 344 could be part of the automated laboratory 320. For example, a liquid chromatography instrument that is part of the automated laboratory 320 could be used as part of the sensor 344 to detect an amount of a substance that is taken in or released by the microorganism (e.g., by detecting an amount of the substance in a sample of growth medium in which the microorganism grows); such a liquid chromatography instrument could also be used to measure an internal characteristic of the microorganism, e.g., by determining an amount of a constituent of the microorganism based on a prepared (e.g., centrifuged and lysed) sample of the microorganism.

The sensor 344 could be configured to detect an amount of a substance taken in by and/or released by the microorganism in the environment of the microorganism. This could include the sensor 344 including electrodes, receptor-containing membranes, imaging systems (e.g., fluorescent imaging systems), contrast agents and/or means for providing contrast agents to a sample, or other means for detecting an amount of an ion, a protein, an antibody, a metabolite, a small molecule, or some other substance in or from the environment of the microorganism. The sensor 344 could be configured to detect an amount of the microorganism at one or more points in time. This could include imaging the microorganism (e.g., counting a number of instances of the microorganism are present in an image of a sample of the microorganism, determining an amount of light absorbed, scattered, reflected, or otherwise interacted with by a sample of the microorganism), weighing and/or determining a volume of the microorganism (e.g., after centrifuging a sample of material that includes the microorganism), or using some other means to determine a volume, mass, number, or other measure of the amount of the microorganism.

The automated laboratory 320 is configured to measure at least one internal characteristic of the microorganism. The automated laboratory 320 could measure such internal characteristics as described elsewhere herein. Such measurements could be performed in intact instances of the microorganism (e.g., a number or amount and/or location of a substance in the microorganism could be determined via fluorescent imaging of the substance in the microorganism), in materials or samples derived from the microorganism (e.g., measuring one or more properties of an enzyme and/or of interactions between the enzyme and other substances using a sample of the enzyme that has been isolated from the microorganism via lysis of membranes of the microorganism, chromatography, or other means), and/or in materials provided by some other source (e.g., from the material stores 350). Further, the automated laboratory 320 could be operated to provide materials for the incubator 340, sensor 344, or other elements of the system 340. This could include preparing substances to provide to the microorganism in the incubator 340 (e.g., metabolites, chemotherapies or other pharmaceuticals, antibodies), preparing substances to modify the genome of microorganisms in the incubator (e.g., providing specified sequences of DNA or RNA, providing viruses or other means for presenting such sequences into the microorganism), generating genetically modified samples of the microorganism to the incubator 340, or preparing some other substances for use by the system 300.

The microscope 320a could be used to image samples of the microorganism and/or to image other materials by a variety of means, e.g., fluorescent imaging, optical light imaging, hyper-resolution imaging, hyperspectral imaging, phase contrast imaging, structured illumination imaging, or some other imaging method. The microscope 320a could be used to determine a number, concentration, amount, distribution, or some other information about a constituent of the microorganism. This could include imaging an intrinsically fluorescent, colored, or otherwise optically detectable substance, adding a fluorophore or other contrast agent that is configured to selectively interact with a substance of interest to a sample of the microorganism and imaging the contrast agent, detecting a degree of absorption, scattering, reflection, or other optical interaction of the microorganism with light at one or more wavelengths, or performing some other imaging process to determine the amount of a constituent in one or more instances of the microorganism. The microscope 320a could be used to determine a degree of interaction between two or more constituents of the microorganism. This could include detecting an amount of Forster energy resonance transfer between two (or more) different constituents of the microorganism in order determine whether instances of the different constituents are in proximity. The microscope 320a could be used to determine some other information about internal or external characteristics of the microorganism.

The separator 320b could be used to separate components of a sample to facilitate a variety of applications. This separation could include separating the contents of one or more instances of the microorganism, e.g., to separate a particular constituent from the rest of the contents of the microorganism. Such separated substances can then be used by the system 300 to perform some functions, e.g., to determine properties of an enzyme, protein, or other separated substance. The separator 320b could include a variety of apparatus for separating the contents of a sample by one or more means. For example, the separator 320b could include a liquid or gas chromatography column. The separator 320b could include a centrifuge, filters, sieves, distillation means, or other apparatus for separating substances within a sample form each other according to one or more physical variables. The separator 320b could include substances (e.g., proteins, antibodies) configured to selectively bind to or otherwise interact with a substance of interest, and such substances could be used to separate one or more constituents of interest from a sample (e.g., using an enzyme-linked immunosorbent assay). The separator 320b could include means for performing electrophoresis of a substance, e.g., for performing electrophoresis on a plurality of segments of DNA or RNA from one or more instances of the microorganism. The separator 320b could include means for performing mass spectrometry of a sample.

The separator 320b could additionally or alternatively be used to measure some property of a sample. For example, a chromatography column of the separator 320b could be used to measure a relative amount of one or more constituents of a sample applied to the chromatography column to be separated. The separator 320b could include additional or alternative means for separating content of a sample, e.g., of a sample including the microorganism.

As shown, the automated laboratory 320 includes a microscope 320a and a separator 320b, but in practice the automated laboratory 320 may include additional or alternative elements. For example, the automated laboratory 320 could include an incubator or other means for performing polymerase chain reactions to increase an amount of a sample of DNA or RNA, means for performing gel electrophoresis or other means for sequencing a sample of DNA or RNA or determining some other information about properties of such a sample, or some other means for determining information about a sample of DNA or RNA. For example, the automated laboratory 320 could include means for measuring a number of instances of one or more specified sequences of RNA that are present in one or more instances of the microorganism (e.g., by performing the multiplication and other processes above, by tagging the one or more specified sequences with a fluorophore or other contrast agent and imaging the one or more instances of the microorganism). The automated laboratory 320 could include a calorimeter, e.g., to measure an amount of energy emitted by one or more chemical processes. The automated laboratory 320 could include means for performing X-ray crystallography, atomic force microscopy, or other means for characterizing the geometry of a protein or other constituent of the microorganism. The automated laboratory 320 could include other apparatus configured to measure additional or alternative properties of a microorganism and/or of constituents thereof.

Controller 310 may be provided as a computing device that includes one or more processors 310a. The one or more processors 310a can be configured to execute computer-readable program instructions that are stored in a computer readable data storage 310b and that are executable to provide the functionality of a system 300 as described herein. Elements of the controller 310 could be implemented as part of a cloud computing system, a server, or some other computing system(s) that are not co-located with other elements of the system 300 (e.g., elements of the controller 300 could be physically distant from the incubator 340, sensor 344, automated laboratory 320, laboratory robot 330, and/or material stores 350). For example, elements of the controller 310 configured and/or programmed to update a model of the microorganism, to determine sets of environmental parameters and/or genetic modifications to which to subject the microorganism, sets of parameters of the model to investigate using the automated laboratory 320, or to perform other processes related to updating the model and/or planning experiments could be implemented as part of a cloud computing service and/or as a server. Other elements of the controller 310, configured and/or programmed to operate the incubator 340, sensor 344, automated laboratory 320, laboratory robot 330, material stores 350, or other elements of the system 300 could be located proximate to those elements of the system 300 and could be in communication with the other elements of the controller 310, e.g., via the Internet.

The computer readable data storage 310b may include or take the form of one or more non-transitory, computer-readable storage media that can be read or accessed by at least one processor 310a. The one or more computer-readable storage media can include volatile and/or non-volatile storage components, such as optical, magnetic, organic or other memory or disc storage, which can be integrated in whole or in part with at least one of the one or more processors 310a. In some embodiments, the computer readable data storage 310b can be implemented using a single physical device (e.g., one optical, magnetic, organic or other memory or disc storage unit), while in other embodiments, the computer readable data storage 310b can be implemented using two or more physical devices.

The program instructions executed by the controller 310 may include instructions to perform any of the methods described herein. For instance, the program instructions could include instructions for controlling the incubator 340 to subject the microorganism to a specified set of environmental conditions during a specified test period. The program instructions could additionally include operating the sensor 344 to obtain one or more measurements indicative of at least one external characteristic of the microorganism during the specified test period. The program instructions could further include accessing a model of the microorganism and determining that at least one parameter of a plurality of adjustable parameters of the model can be adjusted such that the predicted response of the microorganism to the specified set of environmental conditions during the specified test period corresponds to the one or more measurements obtained by the sensor 344. The program instructions could yet further include operating the automated laboratory 330 to measure at least one internal characteristic of the microorganism that relates to the determined at least one parameter of the model of the microorganism. The program instructions could include further instructions, e.g., instructions to operate the laboratory robot 340, material stores 350, or other elements of the system 300 to facilitate an application of the system 300. The program instructions could include instructions to determine the set of specified environmental conditions, to update the model, and/or to apply further sets of environmental conditions to further samples of the microorganism.

V. CONCLUSION

The particular arrangements shown in the Figures should not be viewed as limiting. It should be understood that other embodiments may include more or less of each element shown in a given Figure. Further, some of the illustrated elements may be combined or omitted. Yet further, an exemplary embodiment may include elements that are not illustrated in the Figures.

Additionally, while various aspects and embodiments have been disclosed herein, other aspects and embodiments will be apparent to those skilled in the art. The various aspects and embodiments disclosed herein are included for purposes of illustration and are not intended to be limiting, with the true scope and spirit being indicated by the following claims. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are contemplated herein.

What is claimed is:
1. A system comprising:
an incubator configured to contain a microorganism and to subject the microorganism to one or more environmental conditions that promote or inhibit growth of the microorganism, wherein the growth of the microorganism is associated with the microorganism taking in or releasing a substance;
a sensor coupled to the incubator, the sensor configured to measure at least one external characteristic of the microorganism, wherein the external characteristic includes an amount of the microorganism in the incubator or an amount of the substance in the incubator;
an automated laboratory that is operably coupled to the incubator and is configured to measure at least one internal characteristic of the microorganism, wherein the at least one internal characteristic includes an amount of a constituent within at least one instance of the microorganism or a degree of interaction between the constituent and one or more additional constituents; and
a controller operably coupled to the incubator, to the sensor, and to the automated laboratory, wherein the controller comprises:
a processor; and
a non-transitory computer readable storage medium storing instructions that, when executed by the processor, cause the processor to:
control the incubator to subject the microorganism to a specified set of environmental conditions during a specified test period;
operate the sensor to obtain one or more measurements indicative of the at least one external characteristic of the microorganism during the specified test period;
access a model of the microorganism, wherein the model predicts a response of the microorganism to the specified set of environmental conditions during the specified test period based on a plurality of adjustable parameters, wherein the plurality of adjustable parameters corresponds to a set of internal characteristics of the microorganism;
determine at least one parameter of the plurality of adjustable parameters is to be adjusted based on the predicted response of the microorganism to the specified set of environmental conditions and the one or more measurements obtained by the sensor, wherein the at least one parameter relates to the at least one internal characteristic of the microorganism;

operate the automated laboratory to measure the at least one internal characteristic of the microorganism; and update the model of the microorganism based on the measured at least one internal characteristic of the microorganism.

2. The system of claim 1, wherein controlling the incubator to subject the microorganism to a specified set of environmental conditions during a specified test period comprises controlling the incubator to subject the microorganism to a specified set of environmental conditions during a specified test period, wherein operating the sensor to obtain one or more other measurements indicative of the at least one external characteristic of the microorganism during the specified test period comprises operating the sensor to obtain one or more measurements indicative of the at least one external characteristic of the microorganism during the specified test period, and wherein the computer-readable storage medium further stores instructions for:

controlling the incubator to subject the microorganism to a second specified set of environmental conditions during a second specified test period;

operating the sensor to obtain one or more other measurements indicative of the at least one external characteristic of the microorganism during the second specified test period;

determining that a further at least one parameter of the plurality of adjustable parameters of the updated model is to be adjusted based on a predicted response of the microorganism to the second specified set of environmental conditions and the one or more other measurements obtained by the sensor during the second specified test period, wherein the further at least one parameter of the updated model relates to the further at least one internal characteristic of the microorganism; and operating the automated laboratory to measure the further at least one internal characteristic of the microorganism.

3. The system of claim 1, wherein the computer-readable storage medium further stores instructions for:

detecting external-characteristic data indicating that the microorganism released the substance;

determining, based on the updated model, a modification of the specified set of environmental conditions to increase an amount of the substance produced by the microorganism; and controlling the incubator to subject the microorganism to the determined modified set of environmental conditions during a further test period.

4. The system of claim 1, wherein the computer-readable storage medium further stores instructions for:

detecting external-characteristic data indicating that the microorganism released the substance;

determining, based on the updated model, a modification of a genome of the microorganism to increase an amount of the substance produced by the microorganism; and outputting an indication of the modified genome.

5. The system of claim 1, wherein the computer-readable storage medium further stores instructions for:

controlling the incubator to subject a second sample of the microorganism to a second specified set of environmental conditions during a second specified test period; and operating the sensor to obtain one or more other measurements indicative of the at least one external characteristic of the second sample of the microorganism during the second specified test period, wherein the determination that at least one parameter of the plurality of adjustable parameters is to be adjusted is further based on a predicted response of the microorganism to the second specified set of environmental conditions and the one or more other measurements obtained by the sensor of the second sample.

6. The system of claim 5, wherein the specified set of environmental conditions and the second specified set of environmental conditions differ.

7. The system of claim 5, wherein the sample of the microorganism and the second sample of the microorganism differ with respect to a genome of the microorganism.

8. The system of claim 1, wherein the automated laboratory is configured to measure an amount of a substance in the microorganism using one or more fluorescent imaging techniques.

9. The system of claim 1, wherein the automated laboratory comprises a microscope that is operable to determine a number of instances of a constituent of the microorganism that are present in one or more instances of the microorganism.

10. The system of claim 1, wherein the automated laboratory is configured to measure a number of instances of one or more specified sequences of RNA that are present in one or more instances of the microorganism.

11. The system of claim 1, wherein the automated laboratory is configured to separate contents of one or more instances of the microorganism.

12. A method comprising:

accessing a system that includes:
an incubator;
a sensor coupled to the incubator;
an automated laboratory that is operably coupled to the incubator; and
a controller operably coupled to the incubator, to the sensor, and to the automated laboratory, wherein the controller includes a processor and a non-transitory computer readable storage medium storing instructions;

controlling, using the processor, the incubator to subject a microorganism, in an incubator, to a specified set of environmental conditions that promote or inhibit growth of the microorganism during a specified test period, wherein growth of the microorganism is associated with the microorganism taking in or releasing a substance, wherein each instance of the microorganism includes a plurality of constituents;

operating, using the processor, the sensor to obtain one or more measurements indicative of at least one external characteristic of the microorganism during the specified test period, wherein the sensor is coupled to the incubator, and wherein the at least one external characteristic includes an amount of the microorganism in the incubator or an amount of the substance in the incubator;

accessing, using the processor, a model of the microorganism, wherein the model predicts a response of the microorganism to the specified set of environmental conditions during the specified test period based on a plurality of adjustable parameters;

determining, using the processor, that at least one parameter of the plurality of adjustable parameters can be adjusted such that the predicted response of the microorganism to the specified set of environmental conditions during the specified test period corresponds to the one or more measurements obtained by the sensor, wherein the at least one parameter relates to at least one internal characteristic of the microorganism, and wherein the at least one internal characteristic includes an amount of one of the constituents within at least one instance of the microorganism or a degree of interaction between two or more of the constituents;

operating, using the processor, the automated laboratory to measure the at least one internal characteristic of the microorganism; and updating, using the processor, the model of the microorganism based on the measured at least one internal characteristic of the microorganism.

13. The method of claim 10, wherein subjecting a microorganism to a specified set of environmental conditions that promote or inhibit growth of the microorganism during a specified test period comprises subjecting the microorganism to a specified set of environmental conditions during a specified test period, wherein operating a sensor to obtain one or more measurements indicative of at least one external characteristic of the microorganism during the specified test period comprises operating the sensor to obtain one or more measurements indicative of the at least one external characteristic of the microorganism during the specified test period, and wherein the method further comprises:

subjecting the microorganism to a second specified set of environmental conditions during a second specified test period;

operating the sensor to obtain one or more other measurements indicative of the at least one external characteristic of the microorganism during the second specified test period;

determining that a further at least one parameter of the plurality of adjustable parameters of the updated model is to be adjusted based on a predicted response of the microorganism to the second specified set of environmental conditions and the one or more other measurements obtained by the sensor during the second specified test period, wherein the further at least one parameter of the updated model relates to the further at least one internal characteristic of the microorganism; and operating the automated laboratory to measure the further at least one internal characteristic of the microorganism.

14. The method of claim 10, further comprising:

detecting external-characteristic data indicating that the microorganism released the substance;

determining, based on the updated model, a modification of the specified set of environmental conditions to increase an amount of the substance produced by the microorganism; and subjecting the microorganism to the determined modified set of environmental conditions during a further test period.

15. The method of claim 10, further comprising:

detecting external-characteristic data indicating that the microorganism released the substance;

determining, based on the updated model, a modification of a genome of the microorganism to increase an amount of the substance produced by the microorganism; and subjecting a sample of the microorganism having the modified genome, in the incubator, to the specified set of environmental conditions during a further test period.

16. The method of claim 12, further comprising:

subjecting a second sample of the microorganism to a second specified set of environmental conditions during a second specified test period; and operating the sensor to obtain one or more other measurements indicative of the at least one external characteristic of the second sample of the microorganism during the second specified test period, wherein the determination that at least one parameter of the plurality of adjustable parameters is to be adjusted is further based on a predicted response of the second sample of the microorganism to the second specified set of environmental conditions and to the one or more other measurements obtained by the sensor of the second sample.

17. The method of claim 16, wherein the specified set of environmental conditions and the second specified set of environmental conditions differ.

18. The method of claim 16, wherein the sample of the microorganism and the second sample of the microorganism differ with respect to a genome of the microorganism.

* * * * *